US012788326B2

(12) United States Patent
Lecourt et al.

(10) Patent No.: US 12,788,326 B2
(45) Date of Patent: Nov. 10, 2026

(54) CONNECTION TRANSMITTER WITH CONNECTION BLADES

(71) Applicant: SENSOME, Massy (FR)

(72) Inventors: Guillaume Lecourt, Massy (FR); Gor Lebedev, Massy (FR); Bruno Carreel, Massy (FR)

(73) Assignee: SENSOME, Massy (FR)

( * ) Notice: Subject to any disclaimer, the term of this patent is extended or adjusted under 35 U.S.C. 154(b) by 356 days.

(21) Appl. No.: 18/684,774

(22) PCT Filed: Aug. 12, 2022

(86) PCT No.: PCT/EP2022/072669
§ 371 (c)(1),
(2) Date: Feb. 19, 2024

(87) PCT Pub. No.: WO2023/020961
PCT Pub. Date: Feb. 23, 2023

(65) Prior Publication Data
US 2024/0350089 A1 Oct. 24, 2024

(30) Foreign Application Priority Data
Aug. 20, 2021 (EP) .................................... 21306130

(51) Int. Cl.
*A61B 5/00* (2006.01)
*A61M 25/09* (2006.01)
*H01R 12/75* (2011.01)

(52) U.S. Cl.
CPC ...... *A61B 5/6851* (2013.01); *A61B 2562/227* (2013.01); *A61M 25/09* (2013.01); *H01R 12/75* (2013.01)

(58) Field of Classification Search
CPC ............ A61B 5/6851; A61B 2562/227; H01R 12/75; H01R 12/718; H01R 4/2416; H01R 13/71
(Continued)

(56) References Cited

U.S. PATENT DOCUMENTS 5,023,520 A * 6/1991 Costa ..................... H05B 41/02 361/674
6,428,336 B1 * 8/2002 Akerfeldt ............... H01R 13/59 439/805
(Continued)

FOREIGN PATENT DOCUMENTS

CN 108232548 A * 6/2018 ......... H01R 13/6278
JP 2006-136723 A 6/2006
JP 2012-524975 A 10/2012

OTHER PUBLICATIONS

International Search Report and Written Opinion from the International Searching Authority from corresponding PCT Application No. PCT/EP2022/072669, dated Nov. 30, 2022, By: Authorized Officer: Morten Trachterna.
(Continued)

*Primary Examiner* — Marcus E Harcum
(74) *Attorney, Agent, or Firm* — Andrew J. Tibbett; Greenberg Traurig, LLP

(57) ABSTRACT

Connection transmitter for connecting a guidewire to a connector assembly (14), comprising: —a casing (16) surrounding at least partially the connector assembly, —a longitudinal connecting element (18) extending inside the casing along a longitudinal axis (X). The connecting element is translatable along a transversal axis, and receives the guidewire. The connector assembly comprises at least one connection blade extending along the transversal axis, and the connecting element comprises at least one transversal cavity (26) for receiving the guidewire, and cooperates with
(Continued)

the connection blade. The connection transmitter presents: —a non-connecting configuration, in which the transversal cavity (26) and the connection blade are transversely disengaged, —a connecting configuration, in which the transversal cavity (26) and the connection blade are transversely cooperating by engagement. The connecting configuration enables to connect the guidewire with the at least connection blade.

35 Claims, 6 Drawing Sheets

(58) Field of Classification Search
USPC .......................................................... 439/694
See application file for complete search history.

(56) References Cited

U.S. PATENT DOCUMENTS 6,932,517 B2 * 8/2005 Swayze ................ G02B 6/3891 385/75
7,303,444 B2 * 12/2007 Denpouya ............ H01R 13/629 439/694
9,246,260 B2 * 1/2016 Naganawa ........... H01R 13/516
9,735,484 B2 * 8/2017 Brubaker ............. H01R 43/205
10,199,751 B1 * 2/2019 Gelderd .................. F16F 1/028
11,251,552 B2 * 2/2022 Gruber ................... H01R 43/18
2004/0186542 A1 9/2004 Van Venrooij et al.
2006/0099834 A1 5/2006 Tulkki
2010/0273355 A1 10/2010 Gleason et al.
2014/0120786 A1 * 5/2014 Bishop ................. H01R 12/515 439/878
2014/0180139 A1 6/2014 Millett et al.
2014/0180256 A1 6/2014 Millett
2017/0100054 A1 4/2017 Tai et al.
2017/0237190 A1 * 8/2017 Liao ....................... H01R 12/79 439/64

OTHER PUBLICATIONS

Japanese Office Action dated Jun. 16, 2026, from corresponding Japanese Patent Application 2024-510223 (6 pages).

* cited by examiner

CONNECTION TRANSMITTER WITH CONNECTION BLADES

CROSS-REFERENCE TO RELATED APPLICATIONS

This application is the U.S. National Stage application, pursuant to 35 U.S.C. § 371, of PCT International Patent Application No. PCT/EP2022/072669, filed Aug. 12, 2022, designating the United States and published in English, which claims priority under 35 U.S.C. §§ 119 and 365 to European Patent Application No. 21306130.2, filed Aug. 20, 2021. The contents of each of the aforementioned applications are incorporated herein by reference in their entirety.

FIELD OF INVENTION

The present invention relates to safely connecting a guidewire to a connector, for example a circuit board assembly.

BACKGROUND OF INVENTION

Guidewire assemblies comprising guidewire with a sensor mounted at its distal tip are routinely used in intravascular imaging. The sensor of the distal tip of the guidewire is usually connected to an interface cable, connecting to external equipment such as for example monitors, control units or computers.

Blockages of blood vessels (including veins or arteries) may occur in various parts of an animal (e.g., a human or a non-human animal) and may have significant repercussions. In an ischemic stroke, for example, a blood clot fully or partially blocks blood flow in a cerebral artery. If the clot is not treated quickly, insufficient blood flow may cause irreparable damage to the brain.

Blockages may be caused by blood clots, which may be caused by coagulation of red and/or white blood cells and/or platelets within a blood vessel. The coagulation may be triggered by a variety of factors, including an injury, abnormal blood flow at the site of the blockage, a disease/condition predisposing an animal to coagulation, and/or other factors.

A common treatment of a clot is chemical dissolution of the clot, which is feasible within the first 4.5 hours following blockage of a blood vessel. Another common option is mechanical thrombectomy, in which an aspiration catheter or a stent-retriever is used to remove the blood clot from the blood vessel.

Stent-retrievers include a stent attached at the end of a wire. The stent is deployed into the vasculature and into the clot, expanded into the clot, and, after a typical waiting time of 0.5 to 10 minutes, extracted to pull the clot out of the blood vessel. Due to non-optimal grabbing of the clot by the stent-retriever, some parts of the clot may be left by or be lost from the retriever, such that several succession treatments (an average 3 times) may be necessary to treat the blockage and restore circulation in the vessel.

An early determination of the nature of the clot, performed using a guidewire as describe above, may result in an enhanced treatment of said clot. A known technique for determining the nature of the clot includes applying the sensor assembly of the guidewire to the clot, in order to measure an evolution of the clot impedance over a predetermined frequency range. The corresponding electrical signals are conveyed along the length of the guidewire, which is connected, at its proximal end, to a processing unit, through a connection transmitter.

Document U.S. Pat. No. 6,428,336 discloses a known connection transmitter. This transmitter comprises a series of electrical contacts arranged along a longitudinal axis. The proximal end of the guidewire is inserted along said longitudinal axis, until each electrical contact of the connection transmitter is in electrical contact with a corresponding guidewire contact, said guidewire contacts being successively arranged along a longitudinal direction of the guidewire, at a distance from each other.

However, such device is not satisfactory. Indeed, the operation described above results in greater wear of the guidewire contacts that are closer to the tip of the guidewire, due to the successive friction of the guidewire contacts against the electrical contacts of the connection transmitter. Moreover, handling of the guidewire and the connection transmitter during said connection is cumbersome, for instance due to said friction, which may result in breakage of the guidewire.

Therefore, a purpose of the invention is to provide a connection transmitter that is easier to use than the known connection transmitters, while reducing the risks of deterioration of the guidewire.

SUMMARY

This invention thus relates to a connection transmitter aimed at connecting a guidewire to a connector assembly, the connection transmitter comprising:

- a connector assembly,
- a casing surrounding at least partially the connector assembly,
- a longitudinal connecting element extending inside the casing along a longitudinal axis, wherein the connecting element is translatable, within the casing, along a transversal axis perpendicular to the longitudinal axis, said longitudinal connecting element being further aimed at receiving the guidewire, wherein the connector assembly comprises at least one connection blade extending along the transversal axis, and the connecting element comprises at least one transversal cavity aimed at receiving at least partially the guidewire, and further aimed at cooperating, by transversal translation, with the at least one connection blade, wherein the connection transmitter presents at least two configurations:

- a non-connecting configuration, in which the at least one transversal cavity of the longitudinal connecting element and the at least one connection blade of the connector assembly are transversely disengaged,
- a connecting configuration, in which the at least one transversal cavity of the longitudinal connecting element and the at least one connection blade of the connector assembly are transversely cooperating by engagement, wherein the connecting configuration enables to connect the guidewire introduced inside the longitudinal connecting element with the at least connection blade of the connector assembly.

Thus, this solution achieves the above objective. In particular, it allows the obtaining of a reduction of the wearing of the connection blades and further of a reduced homogeneous wear of said blade while providing an easy and handy connection device.

The connection transmitter according to the invention may include one or more of the following characteristics, taken in isolation from one another or in combination with one another:

- the longitudinal connecting element may comprise a longitudinal cavity extending along the longitudinal axis, said longitudinal cavity being aimed at receiving the guidewire, said longitudinal cavity intersecting each transversal cavity of the longitudinal connecting element,
- the longitudinal connecting element may comprise at least one radial stop configured to prevent radial or transversal motion of the guidewire once said guidewire is introduced in the longitudinal connecting element, only allowing the longitudinal sliding of said guidewire,
- the connecting configuration of the connection transmitter may be obtained by translating the longitudinal connecting element along the transversal axis, thus enabling to connect the guidewire introduced inside the longitudinal connecting element with each connection blade of the connector assembly at the same time,
- the number of connection blades may be equal to the number of transversal cavities such that each connection blade corresponds to a respective transversal cavity,
- the default configuration of the connection transmitter may be the connecting configuration, which is maintained by means of transversal locking element aimed at transversally cooperating with the casing,
- the transversal locking element may comprise a spring aimed at extending between the casing and the longitudinal connecting element,
- the longitudinal connecting element and the casing may both comprise wire longitudinal locking elements aimed at cooperating together when the connection transmitter is in its connecting configuration in order to prevent longitudinal sliding of the introduced guidewire,
- the longitudinal connecting element may comprise an activation switch to switch the longitudinal connecting element between the connecting configuration and the non-connecting configuration, said activation switch being operable from outside the casing,
- the activation switch may comprise a slider aimed at being pushed with a user's thumb.

The invention further relates to a connection kit comprising a connection transmitter according to any one of the hare above listed technical features, and a guidewire aimed at being introduced at least partially inside the connection transmitter.

The connection kit according to the invention may include one or more of the following characteristics, taken in isolation from one another or in combination with one another:

- the connector assembly may comprise N connection blades extending along the transversal axis, and wherein the longitudinal connecting element comprises N transversal cavities, each transversal cavity being aimed at cooperating, by transversal translation, with one corresponding connection blade of the connector assembly, N being an integer equal to a number of contact zones on a proximal end of the guide wire,
- a first end of the guidewire may comprise a series of contact zones arranged along a longitudinal direction of the guidewire, each electrical contact being associated to a respective transversal cavity, a distance along the longitudinal axis between two transversal cavities being equal to a distance, along the longitudinal axis of the guidewire, between the two corresponding contact zones.

The invention further relates to a connection process aimed at connecting a guidewire to a connector assembly of a connection transmitter, the connection process being implemented by means of a connection transmitter according to any one the here-above listed technical features, said connection process comprising following steps in the order of enunciation:

- longitudinally introducing a first end of the guidewire inside the longitudinal connecting element,
- switching the connection transmitter into its connecting configuration, in order to put the guidewire in contact with at least one of the connection blades of the connector assembly.

The process according to the present invention may comprise a step before the introduction of the guidewire inside the longitudinal connecting element, said additional step being the switching of the connection transmitter into its non-connecting configuration.

BRIEF DESCRIPTION OF THE DRAWINGS

The invention will be better understood, and other aims, details, characteristics and advantages thereof will emerge more clearly on reading the detailed explanatory description which follows, of embodiments of the invention given by way of illustration, purely illustrative and non-limiting examples, with reference to the accompanying drawings.

DETAILED DESCRIPTION

Figure 1:
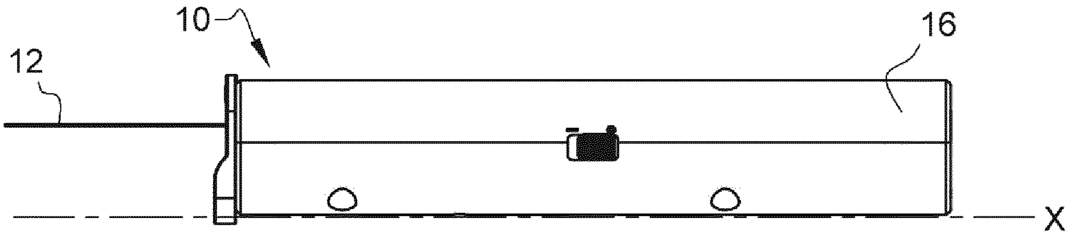
FIG. 1 is a general perspective view of the present invention.

As can be seen on FIG. 1, the present invention relates to a connection transmitter 10 aimed at connecting a guidewire 12 to a connector assembly 14, for example a printed circuit board assembly. The connection transmitter 10 is aimed at being handled by a health professional during operation of the guidewire 12.

Figure 5A:
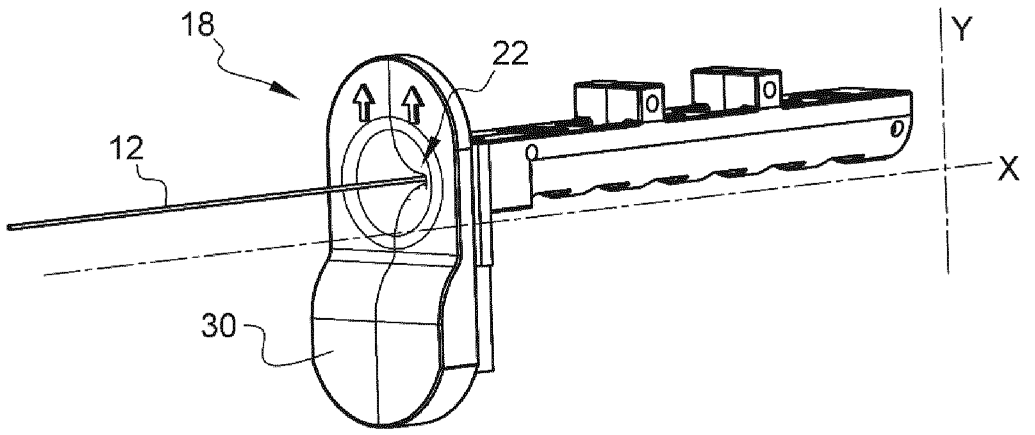
FIGS. 5*a*, 5*b*, are two different views of the longitudinal connecting element of the present invention, respectively a perspective view and a sectional side view.
Figure 5B:
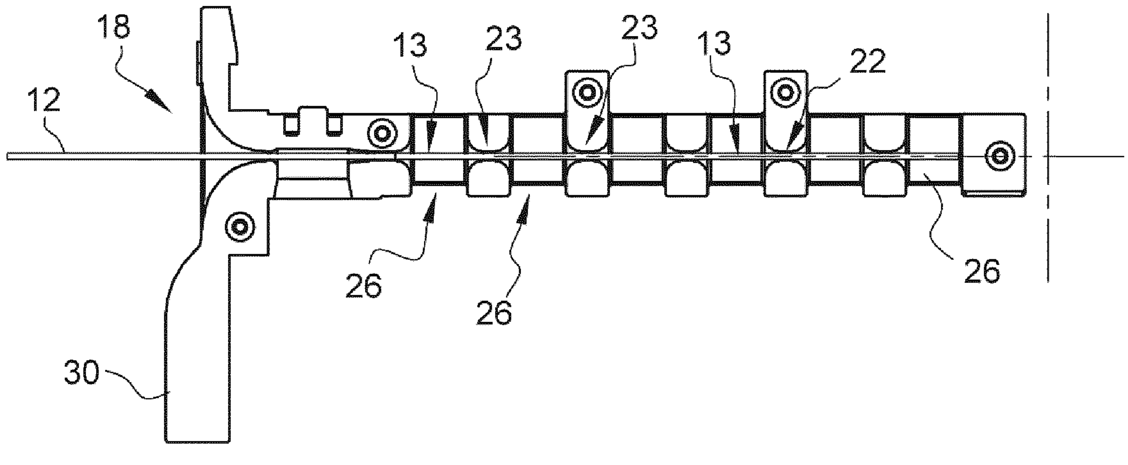

As well known by any person skilled in the art, a guidewire 12 is a wire or spring used as a guide for placement of a larger device or prosthesis, such as a catheter or intramedullary pin, inside a patient's body. The guidewire may also be used to probe tissues of a patient, such as tissues surrounding a clot or the clot itself. The present invention is about connecting a guidewire 12 of about 0.2 to 0.5 mm, preferably 0.35 mm. In this particular intention, the guidewire 12 comprises at least one circumferential contact zone 13 (see FIGS. 5*b* and 8) arranged along a longitudinal direction of the guidewire. Those contact zones are aimed at establishing a connection with the connector assembly 14.

As shown on the figures, the connection transmitter 10 according to the present invention comprises:

- a connector assembly 14, in this case a printed circuit board assembly,
- a casing 16 which preferably extends along a longitudinal axis X,
- a longitudinal connecting element 18 extending inside the casing 16 along the longitudinal axis X.

Figure 2:
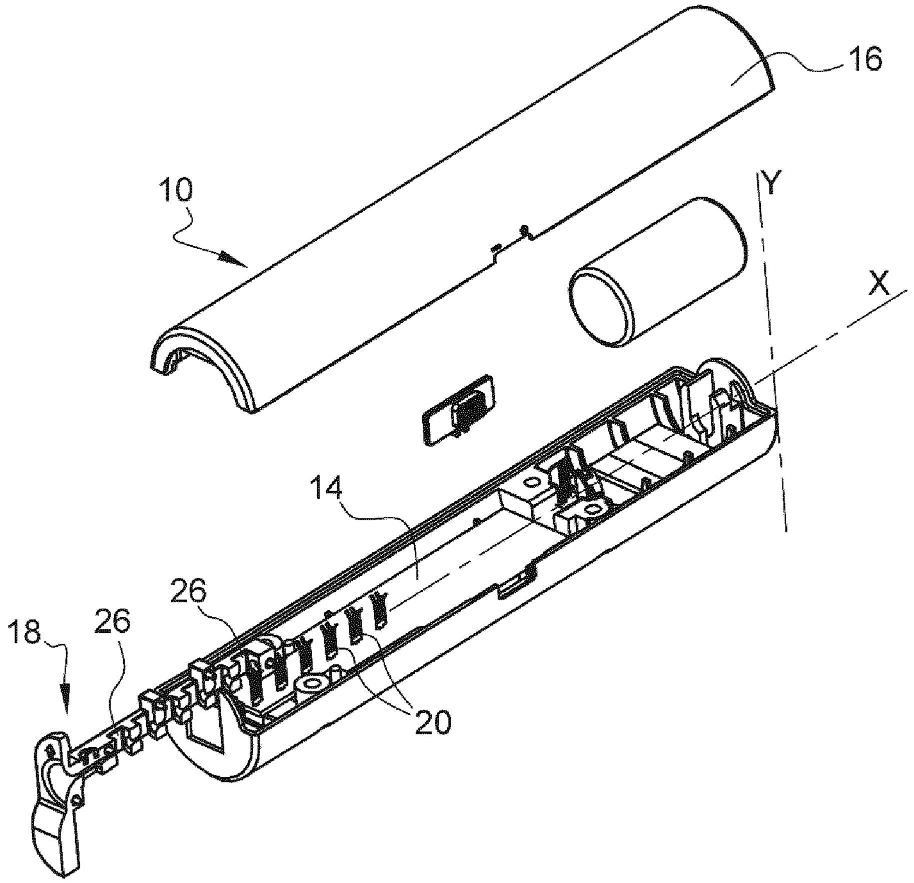
FIG. 2 is an exploded view of the present invention the longitudinal connecting element being outside the casing.
Figure 3:
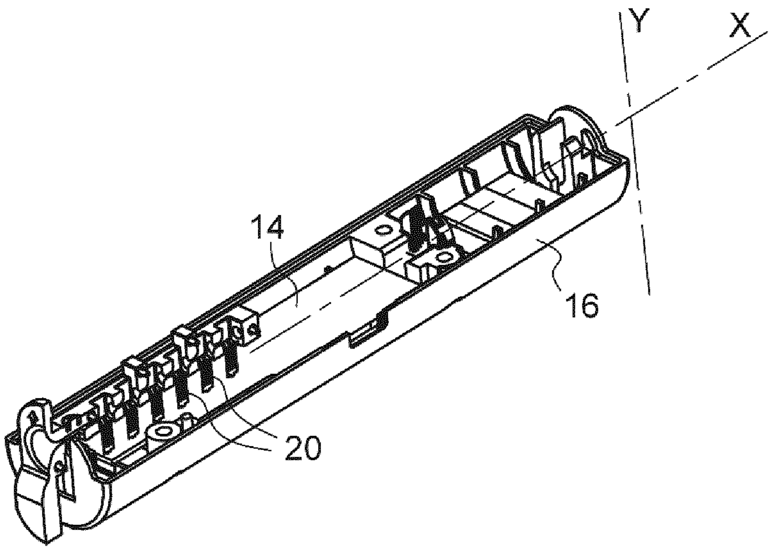
FIG. 3 is an exploded view of the present invention the longitudinal connecting element being inside the casing.
Figure 4:
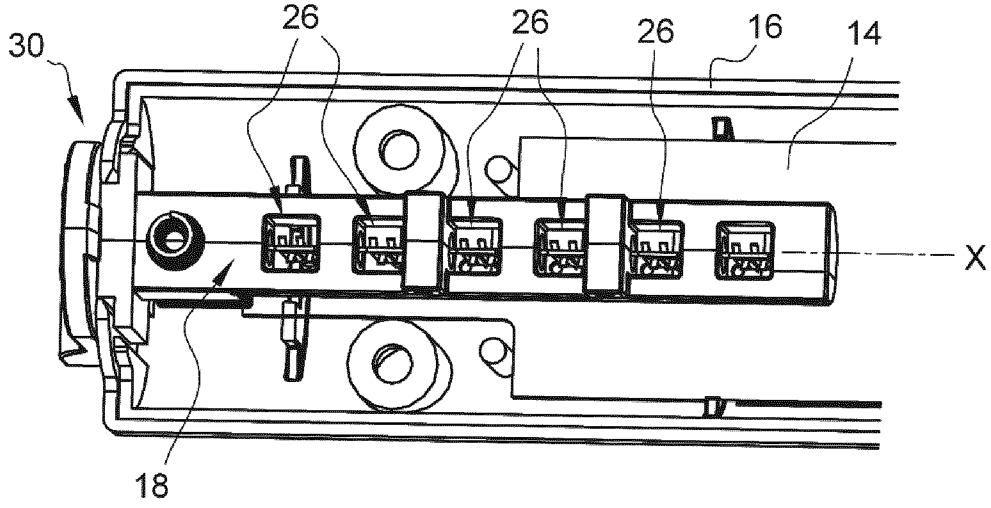
FIG. 4 is an inside perspective view of the present invention.

As can be seen on FIGS. 2, 3 and 4, the casing 16 surrounds at least partially the connector assembly 14. The casing displays a general cylindric shape, as can be seen on FIG. 1. In the embodiment represented on FIGS. 2 and 3, the casing 16 comprises two parts fixed together, for instance screwed together around the connector assembly 14. The casing 16 displays one opening 16*a* at one of its longitudinal extremities, said opening 16*a* receiving the longitudinal connecting element 18.

In some preferred embodiments, the material used for the casing 16 comprises a resin manufactured by FormLabs®: White Resin Standard. It is an ABS-like resin usually used for stereolithography printing. Regarding the size, the casing 16 presents a length comprised between 140 and 150 mm, preferably 148.5 mm and a diameter comprised between 25 and 30 mm, preferably 28 mm.

In some embodiments, the casing 16 is a removable casing.

Figure 6:
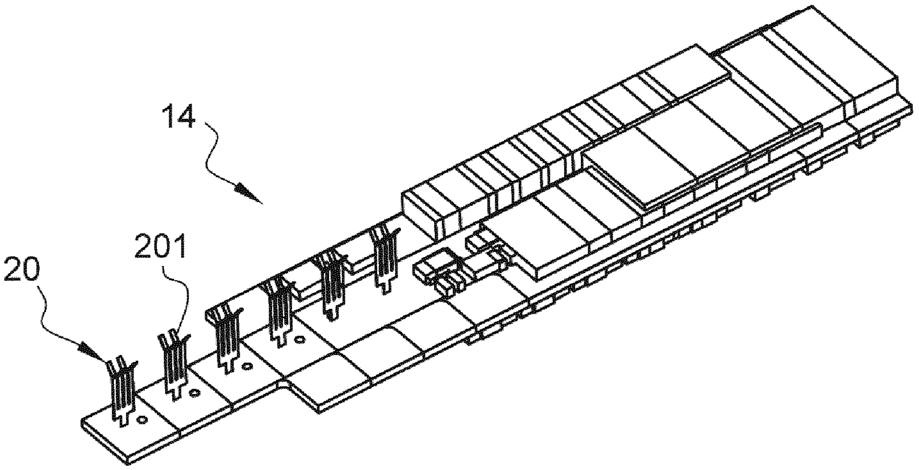
FIG. 6 is a perspective view of a connector assembly according to the invention.

In some embodiments, the connector assembly may be, as illustrated in FIG. 6, a board assembly, and more precisely a printed circuit board assembly (PCBA). Regardless of the embodiment, the size of the connector assembly 14 is dependent on the components used to be functional. Similarly, the shape of the connector assembly 14 is designed according to the guidewire 12 to be connected.

The connector assembly 14 comprises at least one connection blade 20 extending along a transversal axis Y. Each blade 20 is aimed at being put in contact with one corresponding contact zone 13 of the guidewire 12, in order to establish an electrical connection.

The transversal axis Y is sensibly perpendicular to the longitudinal axis X.

Each connecting blade 20 presents a width comprised between 2 and 3 mm, preferably 2.6 mm and a height comprised between 6 and 8 mm, preferably 7.5 mm.

Regarding the present invention, each connection blade 20 comprises at least one finger 201 at its free end. In one embodiment (not represented) the finger may display a general "C" shaped portion either it the extremity of the finger 201 or at its end. The guidewire 12 can cross said C shaped section. In an alternative, not represented embodiment, each finger 201 is simply slightly inclinable and bends under the pressure force exerted by and/or the weight of the guidewire put in contact with it. The finger 201 could also be provided, on its extremity, with a platform aimed at connecting the guidewire 12. On the embodiment illustrated on FIG. 6, each connection blade 20 displays a general comb shape with four fingers 201. More precisely, in this embodiment, the free end of each finger 201 presents a bending in one or the other radial direction. The bending of the fingers 201 alternates along the longitudinally X axis. Those bent fingers 201 thus generate a general V shape of the free ends of each blade 20 which creates a funnel for an introduced guidewire 12.

The blades 20 preferably comprise some kind of copper-beryllium alloy (Cu Be) and are further coated with Nickel (Ni) and Gold (Au) to enhance their electrical properties.

Regarding the illustrated embodiment, the connector assembly 14 comprises six connection blades 20 extending along the transversal axis Y. The six connection blades 20 are aligned along the longitudinal X axis, aligned with the longitudinal connecting element 18 (see FIGS. 2 and 3). More generally, the number of connection blades 20 is at least equal to the number of contact zones 13 of the guidewire with which the connection transmitter 10 is meant to cooperate.

The longitudinal connecting element 18 presents a length comprised between 30 and 50 mm, preferably 42 mm.

The longitudinal connecting element 18 is translatable, within the casing 16, through the opening 16*a*, along the transversal axis Y. The connecting element 18 is longitudinally secured to the casing in order to avoid any unwanted longitudinal sliding along the X axis, as will be later described. When the connection transmitter 10 is functional, the connecting element 18 can only translate transversally along the Y axis.

The longitudinal connecting element 18 is aimed at receiving a guidewire 12. More precisely, as can be seen on FIGS. 5*a* and 5*c*, the longitudinal connecting element 18 comprises a longitudinal cavity 22 extending along the longitudinal axis X. In those embodiments, this longitudinal cavity 22 is aimed at receiving the guidewire 12.

The longitudinal connecting element 18 is specifically designed to avoid radial or transversal sliding of the guidewire 12 once it is introduced in it. More precisely, the longitudinal connecting element 18 only allows the longitudinal sliding of the guidewire 12, as can be deduced from FIGS. 5*a*, 5*b*, 5*c*, 7*a*, 7*b*, 7*c* and 8. In order to achieve this, the longitudinal connecting element 18 comprises at least one radial stop 23. In the embodiment depicted on FIGS. 5*a*, 5*b*, 5*c*, 7*a*, 7*b*, 7*c* and 8, the radial stop 23 is the wall of the longitudinal cavity 22 itself. In some alternative not represented embodiment, the radial stop 23 might be a set of internal teeth or spikes or a specific external wall texture.

Once the guidewire 12 is introduced inside the longitudinal connecting element, it is important that the guidewire remains in place, in all directions. Therefore, in order to further lock the introduced guidewire 12 longitudinally along the X axis, the longitudinal connecting element 18 and the casing 16 both comprise wire longitudinal locking elements 24 aimed at cooperating together when activated. On the depicted embodiment, as can be seen on FIGS. 7*a*, 7*b*, 7*c* and 8, said wire longitudinal locking means comprise a locking block 24*a* secured to the casing 16 while the longitudinal connecting element 18 presents a corresponding transversal locking cavity 24*b*. In some embodiments, locking block 24*a* can be a soft polymer (PDMS) block. Said transversal locking cavity 24*b* opens inside the longitudinal cavity 22 of the longitudinal connecting element 18. The transversal locking cavity 24*b* is stationary with regards to the longitudinal connecting element 18. This way, the transversal locking cavity 24*b* is preferably transversally mobile with respect to the polymer locking block 24*a*. Thus, depending on the transversal position along the Y axis of the longitudinal connecting element 18 inside the casing 16, the polymer locking block 24*a* may be protruding inside the longitudinal cavity 22 of the longitudinal connecting element 18 and obturate it (see FIG. 7*c* and 8) or remain outside said longitudinal cavity 22 (see FIGS. 7*a*, 7*b*). In its protruding position the polymer locking block 24*a* may cooperate by friction with the introduced guidewire 12, thus preventing it from sliding along the X axis.

Advantageously, the longitudinal connecting element 18 further comprises a longitudinal registration element, for instance a distal wall of the longitudinal cavity 22. The longitudinal registration element is designed so that, when the distal tip the guidewire 12 rests against said longitudinal registration element, each contact zone 13 of the guidewire 12 is located in a respective transversal cavity 26 of the longitudinal connecting element 18. Said transversal cavities 26 will be described below.

The longitudinal connecting element 18 further comprises at least one transversal cavity 26 extending along the Y axis. This at least one transversal cavity 26 is aimed at cooperating, by transversal translation, with the at least one connection blade 20 of the connector assembly 14. The number of connection blades 20 is preferably the same as the number of transversal cavities 26. This way, each connection blade 20 corresponds to one corresponding transversal cavity 26. For example, on the embodiment illustrated on FIG. 4, the longitudinal connecting element 18 comprises six transversal cavities 26, each transversal cavity 26 corresponding to a connecting blade 20 with which it is aimed to cooperate. Each cavity presents two openings along the Y axis, on each surface of the longitudinal connecting element 18. In an alternative embodiment, each transversal cavity 26 presents only one opening on the surface facing the connector assembly 14. The transversal cavities are preferably square shaped. The size of each transversal cavity 26 is comprised between 2 and 5 mm length or width. In case the transversal cavities 26 are squares, they preferably measure 4 mm width and 4 mm length, meaning that, when connected to the guidewire 12, each transversal cavity 26 extends 2 mm on each side of the guidewire 12, each half transversal cavity 26 having a width of 2 mm and a length of 4 mm.

Figure 5C:
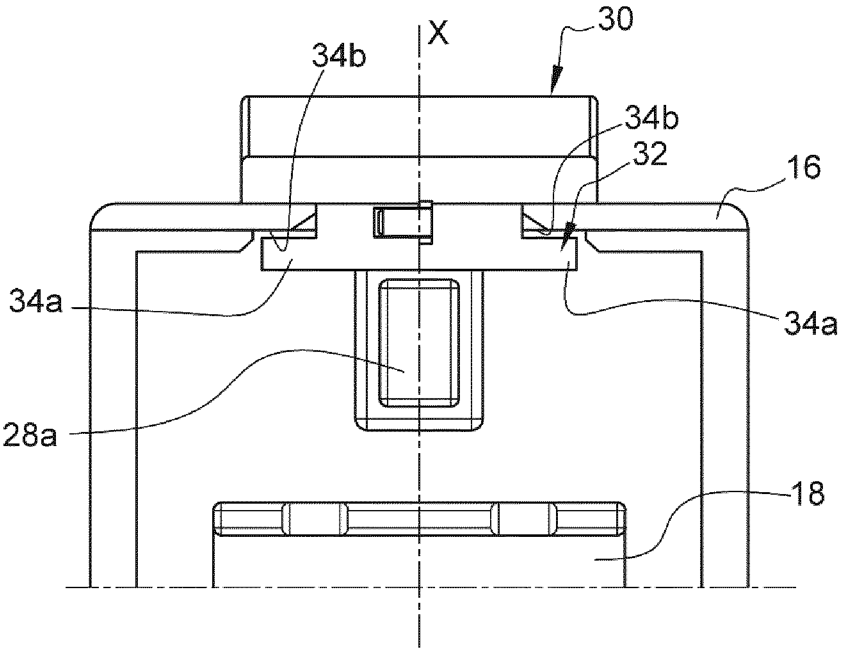
FIG. 5*c* is a sectional transverse view of a slider according to the present invention.
Figure 7A:
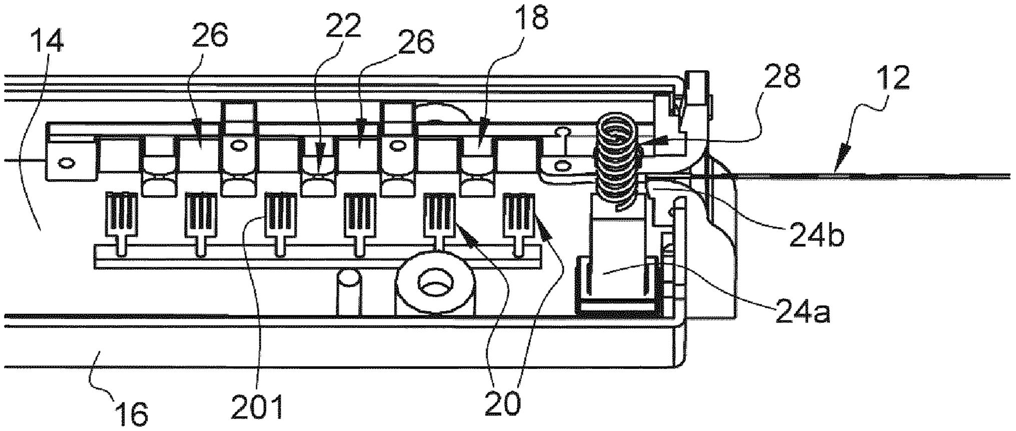
FIGS. 7*a*, 7*b*, 7*c* is a three steps view of the process of connecting a guidewire to a connector assembly by means of the present invention.
Figure 7C:
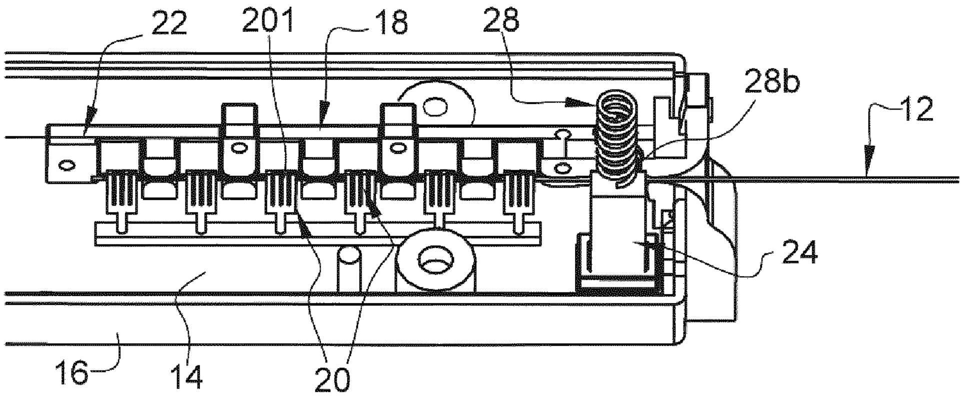
Figure 8:
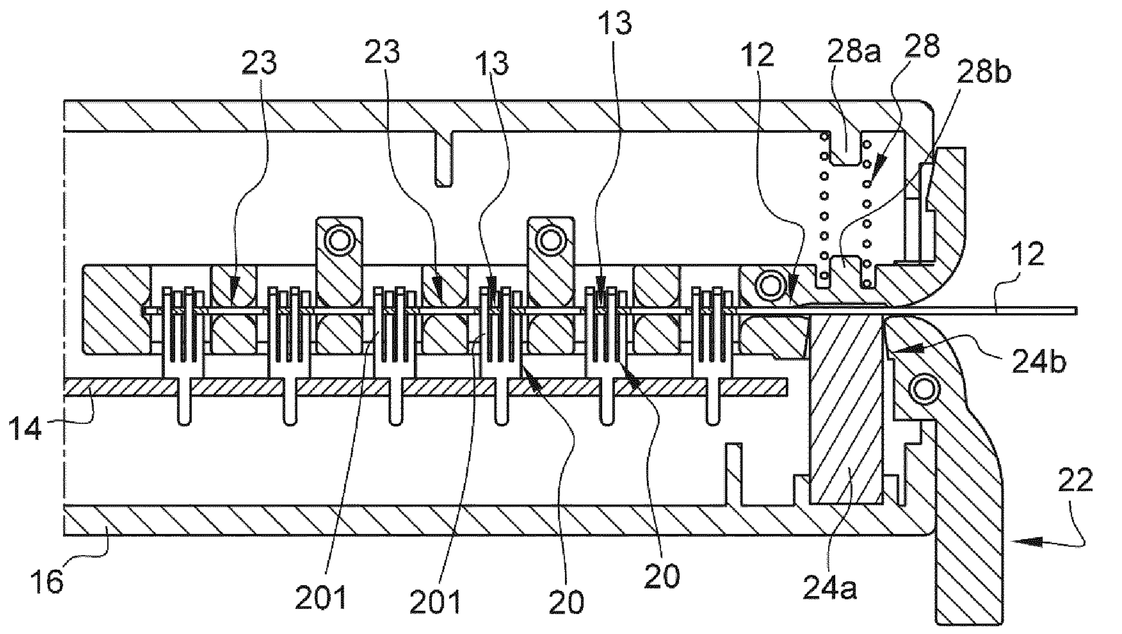
FIG. 8 is a sectional side view of a guidewire connected to a connector assembly by means of the present invention.

As can be seen on FIGS. 7*a* and 8, the longitudinal cavity 22 of the longitudinal connecting element 18 intersects each of its transversal cavity 26 (see FIG. 5*c*). This means that a guidewire 12 introduced into the longitudinal cavity 22 of the longitudinal connecting element 18 may cross each of the transversal cavities 26 of the longitudinal connecting element 18 as illustrated on FIGS. 5*c*, 7*c* and 8.

Figure 7B:
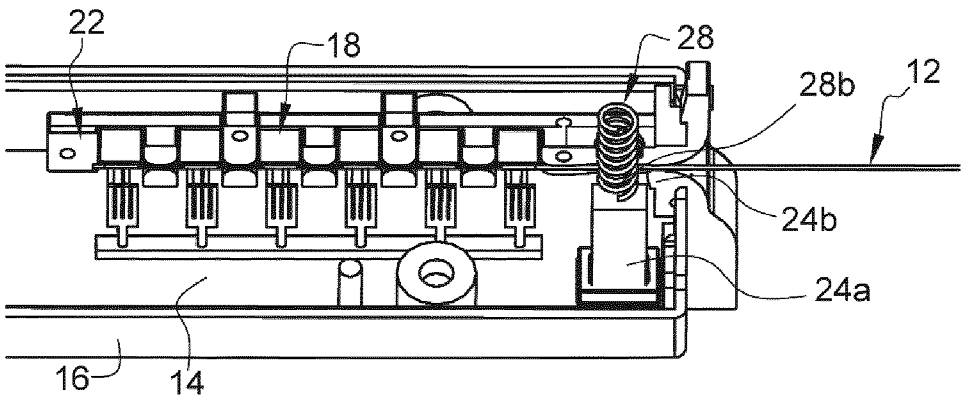

As can be seen on FIGS. 7*a*, 7*b* and 7*c*, the connection transmitter 10 according to the present invention presents at least two configurations:

- a non-connecting configuration, in which the transversal cavities 26 of the longitudinal connecting element 18 and the connection blades 20 of connector assembly 14 are transversely disengaged (see FIG. 7*a*),
- a connecting configuration, in which the transversal cavities 26 of the longitudinal connecting element 18 and each corresponding connection blade 20 of the connector assembly 14 are transversely cooperating by engagement (see FIGS. 7*c* and 8).

The configuration of the connection transmitter 10 is changed by translating transversally (along the Y axis) the longitudinal connecting element 18 within the casing 16.

In the non-connecting configuration, the transversal cavities 26 of the longitudinal connecting element 18 and the connection blades 20 of the connector assembly 14 are positioned in two distinct planes, with respect to the transversal axis Y.

In the connecting configuration, the transversal cavities 26 of the longitudinal connecting element 18 and the connection blades 20 of the connector assembly 14 are positioned in the same plane, regarding the transversal axis Y, leading to a transversal cooperation by engagement, at least partially. Thus, if a guidewire 12 is introduced inside the longitudinal connecting element 18 in the non-connecting configuration, the, by transitioning into this connecting configuration, the guidewire 12 is put in contact with at least one of the connecting blades 20 of the connector assembly 14, as the blades 20 fill the space within the transversal cavities 26 crossed by the guidewire 12. This way, the connecting configuration enables to connect the guidewire 12 introduced inside the longitudinal connecting element 18, and more specifically the contact zones 13, with the connection blades 20 of the connector assembly 14. This is illustrated on FIG. 8.

Regarding the wire longitudinal locking elements 24, when the connection transmitter 10 is in its connecting configuration, as explained above, the polymer locking block 24*a* secures the guidewire 12 thanks to friction. However, in case no guidewire 12 has been introduced inside the longitudinal connecting element 18 yet, if the connection transmitter 10 is in its connecting configuration, the polymer locking block 24*a* has a further purpose: preventing a user to insert the guidewire 12 without activating the longitudinal connecting element 18 and sliding it into the non-connecting configuration in which the connection blades 20 are disengaged from the transversal cavities 26. This protects the connecting blades 20 that could be damaged if a lateral stress is applied to them by forcing a wire among them longitudinally (i.e., along the longitudinal axis X) instead of transversally.

One of the main issues of any kind of connection system is the wear of the connecting elements, in particular the asymmetrical wearing of said elements. In order to avoid said asymmetrical wear and ensure a homogeneous wear of the connecting blades 20 of the connector assembly 14, the connecting configuration of the connection transmitter 10 enables to connect any guidewire 12 introduced inside the longitudinal connecting element 18, with each connection blade 20 at the same time. This is made possible by the transversal translation movement of the longitudinal connecting element 18 within the casing 16.

The wire longitudinal locking elements 24 cooperate together when the connection transmitter 10 is in its connecting configuration in order to avoid any longitudinal sliding of the introduced guidewire 12.

In the embodiment shown on the figures, the default, or resting configuration of the longitudinal connecting element 18 is the connecting configuration. In some not represented alternative embodiment, the default or resting configuration could be the non-connecting configuration. The default/resting configuration is maintained by means of a transversal locking element 28 secured to the longitudinal connecting element 18 and aimed at transversally cooperating with the casing 16. In the embodiment depicted on FIGS. 7*a*, 7*b*, 7*c*, the transversal locking element 28 comprises a spring extending between the casing 16 and the longitudinal connecting element 28, thus continually pushing the connecting element 18 towards the casing 16, in a downwards way. The spring is axially locked by means of two pawns 28*a*, 28*b* (see FIG. 8). In those embodiments, in order to deactivate the transversal locking element 28, the spring has to be activated/compressed. Therefore, in those embodiments, when the spring is activated/compressed, the transversal locking element 28 is deactivated/unlocked and the connection transmitter 10 is in its non-connecting configuration. More precisely, when the locking element 28 is deactivated/unlocked, the connecting element 28 can be pushed upwards to the other half of the casing 16. In an alternative embodiment, when said spring is activated/compressed, the transversal locking element 28 is deactivated/unlocked and the connection transmitter 10 is in its connecting configuration.

To allow activation of the longitudinal connecting element 18, the longitudinal connecting element 18 comprises an activation switch 30, said activation switch 30 being operable from outside the casing. More precisely, the activation switch 30 enables to deactivate/unlock the transversal locking element 28 and thus enabling the longitudinal connecting element 18 to translate transversally (along the Y axis), thus leading to a configuration change. In the embodiment depicted on FIGS. 5*a* and 5*b*, the activation switch 30 comprises a slider 32 which is aimed at being activated with a user's thumb. The slider 32 is secured to the connecting element 18. The slider 32 cooperates with the casing 16, particularly the downside of the casing 16 by means of sliding elements 34. The sliding elements 34 may comprise at least one tab 34*a* located on one of the slider 32 and the casing 16 (for instance at the opening 16*a*), and at least one corresponding transversal groove 34*b* located on the other one of the casing 16 and the slider 32, depending on the embodiment. Each tab 34*a* is aimed at sliding inside its corresponding transversal groove 34*b*, thus allowing the slider 32 to slide transversally with regards to the casing 16, and thus allowing the connected element 18 to slide transversally inside the casing 16.

The connection transmitter 10 according to the present invention enables to implement a connection process aimed at connecting a guidewire 12 to a connector assembly 14 of said connection transmitter 10. With regards to the represented embodiments, the connection process comprises following steps in the order of enunciation:

- switching of the connection transmitter 10 into its non-connecting configuration by means of the activation switch 30,
- longitudinally introducing a guidewire 12 inside the longitudinal cavity 22 of the connecting element 18,
- switching the connection transmitter 10 into its connecting configuration, in order to put the guidewire 12 in contact with at least one of the connection blades 20 of the connector assembly 14.

In some alternative embodiment in which the default/resting configuration is the non-connecting configuration, the first step would not exist.

The invention claimed is:

1. A connection transmitter to connect a guidewire to a connector assembly, the connection transmitter comprising:

a connector assembly;

a casing surrounding at least partially the connector assembly; and a longitudinal connecting element extending inside the casing along a longitudinal axis, wherein the longitudinal connecting element is translatable, within the casing, along a transversal axis perpendicular to the longitudinal axis, the longitudinal connecting element being further aimed at receiving the guidewire, wherein the connector assembly comprises at least one connection blade extending along the transversal axis, and the longitudinal connecting element comprises at least one transversal cavity aimed at receiving at least partially the guidewire, and further aimed at cooperating, by transversal translation, with the at least one connection blade, wherein the connection transmitter presents at least two configurations:

a non-connecting configuration, in which the at least one transversal cavity of the longitudinal connecting element and the at least one connection blade of the connector assembly are transversely disengaged; and a connecting configuration, in which the at least one transversal cavity of the longitudinal connecting element and the at least one connection blade of the connector assembly are transversely cooperating by engagement, and wherein the connecting configuration enables to connect the guidewire introduced inside the longitudinal connecting element with the at least one connection blade of the connector assembly.

2. The connection transmitter of claim 1, wherein the longitudinal connecting element comprises a longitudinal cavity extending along the longitudinal axis, the longitudinal cavity being aimed at receiving the guidewire, the longitudinal cavity intersecting each transversal cavity of the longitudinal connecting element.

3. The Connection transmitter of claim 1, wherein the longitudinal connecting element comprises at least one radial stop configured to prevent radial or transversal motion of the guidewire once the guidewire is introduced in the longitudinal connecting element, only allowing longitudinal translating of the guidewire.

4. The connection transmitter of claim 1, wherein the connecting configuration of the connection transmitter is obtained by translating the longitudinal connecting element along the transversal axis, thus enabling to connect the guidewire introduced inside the longitudinal connecting element with each connection blade of the connector assembly at a same time.

5. The connection transmitter of claim 1, wherein a number of connection blades is equal to a number of transversal cavities such that each connection blade corresponds to a respective transversal cavity.

6. The connection transmitter of claim 1, wherein a default configuration of the connection transmitter is the connecting configuration, which is maintained by means of transversal locking element aimed at transversally cooperating with the casing.

7. The connection transmitter of claim 6, wherein the transversal locking element comprises a spring aimed at extending between the casing and the longitudinal connecting element.

8. The connection transmitter of claim 7, wherein the longitudinal connecting element and the casing both comprise wire longitudinal locking elements aimed at cooperating together when the connection transmitter is in the connecting configuration in order to prevent longitudinal sliding of the introduced guidewire.

9. The connection transmitter of claim 1, wherein the longitudinal connecting element comprises an activation switch to switch the longitudinal connecting element between the connecting configuration and the non-connecting configuration, the activation switch being operable from outside the casing.

10. The connection transmitter of claim 2, wherein the activation switch comprises a slider aimed at being pushed with a user's thumb.

11. A connection kit comprising the connection transmitter of claim 1, and a guidewire aimed at being introduced at least partially inside the connection transmitter.

12. The connection kit of claim 11, wherein the connector assembly comprises N connection blades extending along the transversal axis, and wherein the longitudinal connecting element comprises N transversal cavities, each transversal cavity being aimed at cooperating, by transversal translation, with one corresponding connection blade of the connector assembly, N being an integer equal to a number of contact zones on a proximal end of the guidewire.

13. The connection kit of claim 11, wherein a first end of the guidewire comprises a series of contact zones arranged along a longitudinal direction of the guidewire, each electrical contact being associated to a respective transversal cavity, a distance along the longitudinal axis between two transversal cavities being equal to a distance, along the longitudinal axis of the guidewire, between two corresponding contact zones.

14. A connection process aimed at connecting a guidewire to a connector assembly of a connection transmitter, the connection process being implemented by means of the connection transmitter of claim 1, the connection process comprising:

longitudinally introducing a first end of the guidewire inside the longitudinal connecting element; and after the longitudinally introducing, switching the connection transmitter into the connecting configuration, in order to put the guidewire in contact with the at least one connection blade of the connector assembly.

15. The connection process of claim 14, wherein the process comprises, before the longitudinally introducing of the first end of the guidewire inside the longitudinal connecting element, switching of the connection transmitter into the non-connecting configuration.

16. An apparatus, comprising:

a housing;

one or more electrical contacts in the housing; and a guidewire holder comprising:

a cavity in which a guidewire can be disposed; and one or more windows to provide one or more points of access to the guidewire disposed in the cavity, wherein the holder is movable between a first position with respect to the housing, in which the one or more electrical contacts are positioned in the one or more windows and contact the guidewire, and a second position with respect to the housing, in which the one or more electrical contacts are not positioned in the one or more windows and do not contact the guidewire.

17. The apparatus of claim 16, wherein the one or more electrical contacts electrically connect with the guidewire when the holder is in the first position.

18. The apparatus of claim 16, wherein, when the holder is in the second position, the one or more electrical contacts are spaced from the one or more windows in a direction perpendicular to the cavity of the holder.

19. The apparatus of claim 16, wherein the one or more electrical contacts are electrically connected to a circuit board in the housing.

20. The apparatus of claim 16, wherein the holder comprises one or more stops configured to prevent radial movement of the guidewire within the cavity.

21. The apparatus of claim 20, wherein the one or more windows are interposed with the one or more stops.

22. The apparatus of claim 16, wherein the one or more windows extend across a diameter of the cavity.

23. The apparatus of claim 16, wherein the holder comprises an end wall configured to prevent longitudinal movement of the guidewire disposed in the cavity.

24. The apparatus of claim 16, wherein:

the housing comprises a lock;

the holder comprises a pocket configured to receive the lock and to provide a point of access to the guidewire disposed in the cavity; and when the holder is in the first position, the lock is positioned in the pocket and contacts the guidewire disposed in the cavity to restrict movement of the guidewire.

25. The apparatus of claim 16, wherein:

the housing comprises a lock;

the holder comprises a pocket configured to receive the lock; and when the holder is in the first position, the lock is positioned in the pocket and prevents insertion of the guidewire into the cavity of the holder.

26. The apparatus of claim 16, wherein:

the holder comprises a spring configured to cooperate with the housing to bias the holder into the first position; and the holder comprises a switch configured to transition the holder from the first position to the second position.

27. The apparatus of claim 16, wherein:

the holder comprises a spring configured to cooperate with the housing to bias the holder into the second position; and the holder comprises a switch configured to transition the holder from the second position to the first position.

28. A method, comprising:

positioning a guidewire into a cavity of a guidewire holder, wherein the holder comprises one or more windows to provide one or more points of access to the guidewire disposed in the cavity; and moving the guidewire holder from a first position with respect to a housing, in which one or more electrical contacts are not positioned in the one or more windows and do not contact the guidewire, to a second position with respect to the housing, in which the one or more electrical contacts are positioned in the one or more windows and contact the guidewire.

29. The method of claim 28 further comprising, prior to positioning the guidewire into the cavity, moving the holder from the second position to the first position.

30. The method of claim 29, wherein moving the holder from the second position to the first position exposes the cavity, from a lock of the housing, for receiving the guidewire.

31. The method of claim 29, wherein:

the holder comprises a spring configured to cooperate with the housing to bias the holder into the second position; and moving the guidewire holder from the second position to the first position comprises actuating a switch of the holder to overcome a biasing force of the spring.

32. The method of claim 28, wherein:

moving the holder from the first position to the second position positions a lock of the housing in a pocket of the holder;

the pocket is configured to provide a point of access to the guidewire disposed in the cavity; and when the lock is positioned in the pocket and contacts the guidewire disposed in the cavity, the lock restricts movement of the guidewire disposed in the cavity.

33. The method of claim 28, wherein positioning the guidewire into the cavity comprises inserting the guidewire into the cavity until the guidewire contacts an end wall of the cavity.

34. The method of claim 33, wherein inserting the guidewire into the cavity until the guidewire contacts the end wall of the cavity positions one or more contact zones of the guidewire in the one or more windows.

35. The method of claim 28, wherein moving the guidewire holder from the first position to the second position comprises moving the holder in a direction perpendicular to the cavity of the holder.

* * * * *